United States Patent
Mitchell et al.

(10) Patent No.: US 12,410,236 B2
(45) Date of Patent: *Sep. 9, 2025

(54) COMPOSITIONS COMPRISING PCSK9-BINDING MOLECULES AND METHODS OF USE

(71) Applicant: LIB Therapeutics, Inc., Cincinnati, OH (US)

(72) Inventors: Tracy S. Mitchell, Cincinnati, OH (US); Richard Mealey, Cincinnati, OH (US)

(73) Assignee: LIB Therapeutics, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/318,343

(22) Filed: May 16, 2023

(65) Prior Publication Data

US 2023/0295270 A1    Sep. 21, 2023

Related U.S. Application Data

(63) Continuation of application No. 16/934,816, filed on Jul. 21, 2020, now Pat. No. 11,692,021, which is a continuation of application No. 16/578,102, filed on Sep. 20, 2019, now Pat. No. 10,738,102, which is a continuation of application No. PCT/US2019/032710, filed on May 16, 2019.

(60) Provisional application No. 62/672,187, filed on May 16, 2018.

(51) Int. Cl.
*C07K 14/78* (2006.01)
*A61K 38/00* (2006.01)
*A61P 3/06* (2006.01)
*C07K 14/765* (2006.01)
*C07K 16/40* (2006.01)

(52) U.S. Cl.
CPC .............. *C07K 14/78* (2013.01); *A61P 3/06* (2018.01); *C07K 14/765* (2013.01); *C07K 16/40* (2013.01); *A61K 38/00* (2013.01); *C07K 2319/74* (2013.01)

(58) Field of Classification Search
CPC ...... C07K 14/78; C07K 14/765; C07K 16/40; C07K 2319/74; C07K 2317/92; C07K 2317/94; C07K 2318/20; C07K 2319/31; C07K 14/76; A61P 3/06; A61K 38/00; A61K 39/39591; A61K 2039/505; A61K 2039/545

See application file for complete search history.

(56) References Cited

U.S. PATENT DOCUMENTS

| | | | |
|---|---|---|---|
| 7,932,268 B2 * | 4/2011 | Rader | A61K 31/445 |
| | | | 514/321 |
| 8,420,098 B2 | 4/2013 | Camphausen et al. | |
| 9,234,027 B2 | 1/2016 | Camphausen et al. | |
| 9,856,309 B2 | 1/2018 | Camphausen et al. | |
| 10,738,102 B2 * | 8/2020 | Mitchell | C07K 14/765 |
| 10,947,297 B2 * | 3/2021 | Camphausen | A61K 47/60 |
| 11,692,021 B2 * | 7/2023 | Mitchell | A61K 39/39591 |
| | | | 530/300 |
| 2012/0094909 A1 * | 4/2012 | Camphausen | C07K 16/18 |
| | | | 530/387.3 |
| 2013/0302399 A1 | 11/2013 | Feldhaus et al. | |
| 2016/0159883 A1 | 6/2016 | Camphausen et al. | |
| 2018/0105575 A1 | 4/2018 | Pabst et al. | |

FOREIGN PATENT DOCUMENTS

| | | | | |
|---|---|---|---|---|
| WO | WO-2011130354 A1 * | 10/2011 | | A61K 38/39 |
| WO | 2014/140210 A1 | 9/2014 | | |
| WO | 2014/165093 A2 | 10/2014 | | |
| WO | 2015/143199 A1 | 9/2015 | | |
| WO | WO-2015143156 A1 * | 9/2015 | | A61K 47/64 |

OTHER PUBLICATIONS

Tracy Mitchell et al., Pharmacologic Profile of the Adnectin BMS-962476, a Small Protein Biologic Alternative to PCSK9 Antibodies for Low-Density Lipoprotein Lowering, the Journal of Pharmacology and Experimental Therapeutics, Aug. 2014, J Pharmacol Exp Ther 350:412-424, downloaded from jpet.aspetjournals.org at ASPET Journals.

M.H. Parker et al., Antibody Mimics Based on Human Fibronectin Type Three Domain Engineered for Thermostability and High-Affinity Binding to Vascular Endothelial Growth Factor Receptor Two, Protien Engineering, Design & Selection vol. 18 No. 9 pp. 435-444, published online Aug. 8, 2005, by Oxford University Press.

Frederick J. Raal et al., PCSK9 Inhibition-Mediated Reduction in Lp(a) with Evolocumab: An Analysis of 10 Clinical Trials and the LDL Receptor's Role, Journal of Lipid Research vol. 57, 2016, pp. 1086-1096, published by JLR Papers in Press, Apr. 14, 2016.

Esha Sachdev et al., Adnectin-Targeted Inhibitors: Rationale and Results, Curr Oncol Rep (2015) 17:35, published online: Jun. 5, 2015, by Springer Science+Business Media.

International Search Report and Written Opinion for International Application No. PCT/US2019/032710 dated Sep. 11, 2019.

* cited by examiner

*Primary Examiner* — Li N Komatsu (74) *Attorney, Agent, or Firm* — Morgan, Lewis & Bockius LLP

(57) ABSTRACT

The present disclosure provides pharmaceutical compositions comprising fibronectin based scaffold domain proteins that bind, for example, proprotein convertase subtilisin kexin-9 (PCSK9).

8 Claims, 3 Drawing Sheets

Specification includes a Sequence Listing.

FIG. 1

HSA = human serum albumin; PCSK9 = proprotein convertase subtilisin/kexin type 9.

FIG. 2A

LIB003 plasma PK model

FIG. 2B

Gadkar Model

COMPOSITIONS COMPRISING PCSK9-BINDING MOLECULES AND METHODS OF USE

RELATED APPLICATIONS

This Application is a continuation of U.S. patent application Ser. No. 16/934,916 (now U.S. Pat. No. 11,692,021), filed Jul. 21, 2020, which is a continuation of U.S. patent application Ser. No. 16/578,102 (now U.S. Pat. No. 10,738,102), filed on Sep. 20, 2019, which is a continuation of International Application Serial No. PCT/US2019/032710, filed Mary 16, 2019, which claims the benefit of and priority to U.S. Provisional Application No. 62/672,187 filed May 16, 2018, all of which is hereby incorporated by reference in their entirety.

SEQUENCE LISTING

The instant application contains a Sequence Listing which has been submitted in XML format via PatentCenter and is hereby incorporated by reference in its entirety. Said XML copy, created on Mar. 4, 2025, is named LIB-004C3_Sequence_Listing and is approximately 6,627 bytes in size.

FIELD OF THE DISCLOSURE

The disclosure is directed to fibronectin-based scaffold domain proteins that bind proprotein convertase subtilisin kexin type 9 (PCSK9), as well as pharmaceutical compositions thereof and methods of use.

BACKGROUND

Proprotein convertase subtilisin kexin type 9 (PCSK9) is an enzyme encoded by the PCSK9 gene in humans on chromosome 1. PCSK9 binds to the receptor for low-density lipoprotein particles (LDL). The LDL receptor (LDLR), on liver and other cell membranes, binds and initiates endocytosis of LDL-particles from extracellular fluid into cells, thus reducing circulating LDL particle concentrations. If PCSK9 is blocked, more LDLRs are recycled and are present on the surface of cells to remove LDL-particles from the extracellular fluid. Therefore, blocking PCSK9 can lower blood LDL-particle concentrations.

Monoclonal antibody PCSK9 inhibitors, alirocumab and evolocumab, were approved as once every two week or monthly subcutaneous injections or infusions for lowering LDL-particle concentrations when statins and other drugs were not sufficiently effective or poorly tolerated. For monthly injections, several milliliters of drug product are required to reach the desired dose. While formulations having a higher concentration of active agent could provide more desirable dosing schedules and volumes, these are hindered by solubility limitations, increased viscosity and the instability of biologics, including a propensity for aggregation and particulate formation. Carpenter JF, et al., Overlooking subvisible particles in therapeutic protein products: Gaps that may compromise product quality, Journal of Pharmaceutical Sciences Vol. 98, Issue 4 (2008).

Pharmaceutical compositions targeting PCSK9 and having the potential for more desirable dosing schedules, smaller volumes and/or improvements in efficacy while maintaining a generally safe and well-tolerated profile are needed.

SUMMARY

The present disclosure provides compositions comprising fibronectin scaffold proteins that bind proprotein convertase subtilisin kexin type 9 (PCSK9) with high affinity, and which can be stably formulated at high concentrations for maximum biological effect and more convenient dosing schedules, dosing volumes, and patient-friendly delivery devices. The PCSK9-binding fusion protein comprises a PCSK9-binding motif and an amino acid sequence of a human serum albumin (HSA). The PCSK9-binding motif and the HSA amino acid sequence can be expressed as a genetic fusion or chemically conjugated.

The PCSK9-binding motif described herein is based on an adnectin, a protein family derived from human fibronectin-10th-type III-domain (10Fn3), engineered for high-affinity target binding. According to this disclosure, the PCSK9-binding fusion protein is stably formulated at high concentrations, to allow for maximum biological activity, and convenient dosing schedules and volumes. The concentration of the PCSK9-binding fusion protein in the composition is at least 100 mg/mL. In some embodiments, the concentration of the PCSK9-binding fusion protein in the composition is at least about 200 mg/mL. In some embodiments, the concentration of the PCSK9-binding fusion protein in the composition is at least about 250 mg/mL, or at least about 275 mg/mL, or at least about 300 mg/mL, or at least about 350 mg/L. In some embodiments, the PCSK9-binding fusion protein is administered at a unit dose of from about 275 mg to about 325 mg (e.g., about 300 mg).

The PCSK9-binding motif comprises or consists of the amino acid sequence of (SEQ ID NO: 1), or a variant thereof as described herein. The PCSK9-binding motif binds to human PCSK9 with sub-nanomolar affinity in a concentration-dependent manner. The PCSK9-binding motif has a chemical conjugation to, or a C-terminal fusion of, a human serum albumin (HSA) amino acid sequence. In various embodiments, the PCSK9-binding motif has a fusion of the HSA amino acid sequence at the C-terminus, and may comprise a linking sequence of amino acids between the PCSK9-binding motif and the HSA amino acid sequence.

The PCSK9-binding fusion protein can be stably formulated in the form of a solution at high concentration. The formulation does not exhibit substantial degradation or particulate formation at conventional long-term storage conditions and short-term storage under accelerated and stressed conditions. Exemplary formulations comprise or consist essentially of (in addition to the active agent as described): L-Histidine, L-Histidine monohydrochloride, Sodium chloride, and optionally Polysorbate-80.

The pharmaceutical compositions of the disclosure may be conveniently presented in unit dose forms containing a predetermined amount of an active agent of the disclosure per dose. In some embodiments, the unit doses are no more than about 1.5 mL in volume, or no more than about 1 mL in volume. In some embodiments, the unit doses are no more than 0.8 mL in volume, or no more than 0.7 mL in volume. In still other embodiments, the composition is administered as a microdose, for example, with a volume of less than 0.5 mL, or less than about 0.25 mL, or less than about 0.15 mL. In various embodiments, the composition is delivered at a unit dose comprising about 20 to about 450 mg of the PCSK9-binding fusion protein. For example, in some embodiments, a dose of from 20 to about 75 mg is administered as a weekly microdose (e.g., in a volume less than about 0.25 mL or less than about 0.15 mL). In other embodiments, a dose of from about 200 to about 450 mg is administered about every two weeks, monthly, or every other month, with a volume in the range of about 0.7 to 1.5 mL.

The composition or formulation is suitable for administration by subcutaneous, intramuscular, intradermal, or intravenous administration. The high concentration of the formulation allows for less frequent dosing schedules and lower dosing volumes suitable for subcutaneous administration. As demonstrated herein, maximum PCSK9 suppression is achieved at a relatively low concentration of PCSK9-binding fusion protein, and higher concentrations allow for a longer duration of suppression. In some embodiments, the subject receives a unit dose of the composition about once every week, once every 2 weeks, or about once every 3 weeks, or about once every 4 weeks (e.g., about once per month), or about once every 6 weeks, or about once every 8 weeks (about once every 2 months).

In some embodiments, the subject receives a micro dose of the composition, such as a volume of from about 50 to about 250 µL, about every week or about every two weeks.

The composition may be administered for treating a PCSK9-related disorder in a human subject. In some embodiments, the patient is in need of a reduction in LDL (e.g., LDL-C). In some embodiments, the subject may exhibit a cholesterol-related disease such as hypercholesterolemia and/or atherosclerosis. In some embodiments, the subject has familial hypercholesterolemia. In some embodiments, the subject has or is at high risk of cardiovascular disease (e.g., atherosclerotic coronary heart disease).

In some embodiments, the composition is administered alongside statin therapy or another oral lipid lowering therapy, or in some embodiments, the composition is provided as the sole therapy for hypercholesterolemia, that is, without oral lipid lowering therapy (e.g., statin therapy).

DETAILED DESCRIPTION

The present disclosure provides compositions comprising fibronectin scaffold fusion proteins that bind proprotein convertase subtilisin kexin-9 (PCSK9) with high affinity, and which can be stably formulated at high concentration for maximum biological effect and more convenient dosing schedules and dosing volumes, and delivery using patient-friendly delivery devices such as a syringe or autoinjector. The PCSK9-binding fusion protein comprises a PCSK9-binding motif and an amino acid sequence encoding a human serum albumin (HSA) at the C-terminus.

Proprotein convertase subtilisin/kexin type 9 is a circulating protein secreted mainly by the liver that plays a significant role in the recycling of hepatic LDLRs and has been identified as a validated drug target for reduction of LDL-C. The LDLR is the primary pathway for LDL-Cholesterol (LDL-C) clearance from circulation. Plasma PCSK9 binds to the hepatic LDLR along with LDL-C, which targets the receptor for endocytosis and degradation, thus reducing the availability of LDLRs to clear LDL-C from circulation. By inhibiting PCSK9 binding to LDLR, LDLR degradation is prevented, LDLR recycling is increased, LDL-C clearance is enhanced and circulating LDL-C levels are reduced.

The PCSK9-binding motif described herein is based on an "adnectin," a protein family derived from human fibronectin-10th-type III-domain, engineered for high-affinity target binding. "Adnectins" are small (≤12 kDa), compact proteins without sequence homology to immunoglobulins but possessing a β-sheet fold structure with diversified loops analogous to antibody variable regions. Adnectins have no disulfides and are not glycosylated, exhibit high thermal stability and monomeric solution behavior, and are efficiently produced using bacterial, yeast, or mammalian expression systems. By modifying variable loop sequence and length while holding scaffold residues substantially constant, sub-nanomolar target binding affinity can be achieved while structural stability is maintained. Given their size, adnectins are rapidly filtered by the kidney and therefore require pharmacokinetic (PK) enhancement modification for in vivo applications. Exemplary PCSK9-binding motifs (adnectins) are disclosed in U.S. Pat. Nos. 8,420,098; 9,234,027; and 9,856,309, each of which is hereby incorporated by reference in its entirety.

According to this disclosure, the PCSK9-binding fusion protein is stably formulated at high concentration, to allow for maximum biological activity, and convenient dosing schedules and volumes. The concentration of the PCSK9-binding fusion protein in the composition is at least 100 mg/mL. In some embodiments, the concentration of the PCSK9-binding fusion protein in the composition is at least about 150 mg/mL, or in some embodiments, at least about 175 mg/mL, or at least about 200 mg/mL, or at least about 225 mg/mL. In some embodiments, the concentration of the PCSK9-binding fusion protein in the composition is at least about 250 mg/mL, or at least about 275 mg/mL, or at least about 300 mg/mL, or at least about 350 mg/mL. In some embodiments, the concentration of the PCSK9-binding fusion protein in the composition is from about 250 mg/mL to about 350 mg/mL. In some embodiments, the concentration of the PCSK9-binding fusion protein in the composition is about 250 mg/mL or about 300 mg/mL.

The PCSK9-binding motif comprises or consists of the amino acid sequence of (SEQ ID NO: 1):

VSDVPRDLEVVAATPTSLLISW<u>DAPAEGYGYYRI</u>TYGETGGNSPVQEFT

VPV<u>SKGTATI</u>SGLKPGVDYTITVYAV<u>EFDFPGAGYYHRP</u>ISINYRTE.

PCSK9 binding loops are shown underlined. In some embodiments, the PCSK9-binding motif is a variant of SEQ ID NO:1, having from one to five amino acid substitutions, deletions, or insertions with respect to SEQ ID NO:1. In some embodiments, amino acid alterations are made outside the binding loops. In some embodiments, 1, 2, or 3 amino acid alterations are made within binding loops.

The PCSK9-binding motif is designed to specifically target PCSK9 while substantially maintaining the wild-type (WT) [10]Fn3 sequence to minimize inherent immunogenicity. See, U.S. Pat. No. 8,420,098, which is hereby incorporated by reference in its entirety. The PCSK9-binding motif binds to human PCSK9 with sub-nanomolar affinity in a concentration dependent manner.

In various embodiments, the PCSK9-binding motif has a C-terminal fusion of a human serum albumin (HSA) amino acid sequence. In some embodiments, the HSA comprises a sequence having at least 80% identity, or at least 85% identity, or at least 90% identity, or at least 95% identity, or at least 98% identity, or at least 99% identity to the amino acid sequence of SEQ ID NO: 2. For example, the HSA amino acid sequence may comprise from one to ten, or from one to five, modifications independently selected from amino acid substitutions, deletions, and insertions with respect to SEQ ID NO:2. In some embodiments, the HSA amino acid sequence comprises an alanine residue at the position corresponding to position 34 of SEQ ID NO: 2, as illustrated in SEQ ID NO: 2. In various embodiments, the HSA amino acid sequence is at least 500 amino acids in length.

In some embodiments, the PCSK9-binding motif and the HSA amino acid sequence are chemically conjugated using any known chemical conjugation approach.

HSA is a multi-domain protein consisting of helix clusters and contains 17 pairs of disulfide bridges: only one cysteine residue, Cys34, exists as a free sulfhydryl group in the native HSA. In some embodiments, this Cys is substituted with an alanine residue in the PCSK9-binding fusion protein. The HSA moiety serves to enhance the circulating half-life of the PCSK9-binding fusion protein. In various embodiments, the PCSK9-binding fusion protein, comprising the PCSK9-binding motif and HSA amino acid sequence, has a molecular weight of about 77 kDa.

In some embodiments, the HSA amino acid sequence is a variant described in U.S. Pat. Nos. 9,493,545, 9,821,039, 9,944,691, or US 2014/0315817, each of which is hereby incorporated by reference in its entirety.

In some embodiments, the PCSK9-binding motif and the HSA amino acid sequence are linked by genetic fusion, e.g., with the HSA amino acid sequence at the C-terminus of the molecule. A short amino acid linker may join the PCSK9-binding domain and HSA amino acid sequence. For example, the linker may comprise from 2 to 20 amino acids, or in some embodiments, from 4 to 10 amino acids. In some embodiments, the PCSK9-binding motif and the HSA amino acid sequence are linked via a 6 amino acid linker. The linker may be composed predominately of serine, glycine, threonine, and alanine amino acids. For example, the linker may be a serine/glycine linker. In some embodiments, the linker comprises or consists of the amino acid sequence GSGSGS (SEQ ID NO: 4).

The PCSK9-binding fusion protein can be stably formulated in the form of a solution, at high concentration. For example, the formulation does not exhibit substantial degradation or particulate formation under long term storage conditions, such as a temperature of about 5° C. (e.g. from 2 to 8° C.) or short-term storage conditions at ambient conditions (e.g. from 1 to 6 months at 25+3° C.). The PCSK9-binding fusion protein is suspended in an appropriate physiological solution, e.g., saline or other pharmacologically acceptable solvent or a buffered solution, and may optionally comprise a surfactant (e.g., a non-ionic surfactant). In some embodiments, the formulation comprises a buffering agent, an isotonicity agent, optionally a surfactant, and a solvent.

Pharmaceutically acceptable carriers include water, saline, glycerol. In some embodiments, the formulation may comprise fixed oils, polyethylene glycol, propylene glycol or other solvents. In some embodiments, the solvent is water.

The formulation is generally a buffered solution. As used herein, a "buffer" refers to a chemical agent that is able to absorb a certain quantity of acid or base without undergoing a strong variation in pH. Exemplary buffers include citrate buffer, phosphate buffer, acetate buffer, succinate buffer, and bicarbonate buffer. In some embodiments, the buffering agent may comprise L-Histidine/L-Histidine, monohydrochloride. For example, when using the L-Histidine/L-Histidine, monohydrochloride buffering system, L-Histidine/L-Histidine, monohydrochloride may be present at from about 1 mg/mL to about 10 mg/mL, such as from about 2 mg/mL to about 5 mg/mL. In some embodiments, the buffer maintains the pH of the formulation in the range of about pH 5.5 to about pH 7.2, such as about pH 6.8 (e.g., pH 6.6 to 7.0). In some embodiments, the formulation is pH adjusted, e.g., with hydrochloric acid and/or sodium hydroxide. In some embodiments, the ratio of L-Histidine/L-Histidine, monohydrochloride is such as to not require pH adjustment.

In various embodiments, isotonicity agents, which can be used singly or in combination, include dextrose, sucrose, glycerin, trehalose, mannitol, sorbitol, arginine, sodium chloride, or potassium chloride. In some embodiments, the isotonicity agent comprises or consists of sodium chloride. For example, the formulation may comprise from about 2 to about 20 mg/mL of sodium chloride (e.g., from 6 to 12 mg/mL sodium chloride), or one or more isotonicity agents in an amount equivalent to the osmolality of 2 to 20 mg/mL of sodium chloride (or 6 to 12 mg/mL sodium chloride).

In some embodiments, the formulation comprises a surfactant, which can act as a solubilizing agent. In some embodiments, the surfactant is a non-ionic surfactant. Exemplary non-ionic surfactants include polysorbate surfactants, such as polysorbate 20, 40, 60, or 80. For example, the formulation may comprise polysorbate 80. Other pharmaceutically-acceptable non-ionic surfactants may also be employed, singly or in combination. In some embodiments, the formulation does not comprise a surfactant.

Exemplary formulations include citrate buffer (e.g., 10-50 mM, pH 5.6 to 6.0), histidine buffer (e.g., 10 mM to 50 mM, pH 6.0 to 7.0), or succinate buffer (e.g., 10 to 50 mM, pH 5.5 to 6.0). In some embodiments, the formulation comprises an excipient selected from arginine (e.g., 100 to 200 mM), NaCl (e.g., 100 to 200 mM), sorbitol (e.g., 100 to 300 mM), or sucrose (e.g., 100 to 300 mM). In some embodiments, the formulation comprises a surfactant such as polysorbate 80 (e.g., 0.01 to 0.5 mg/mL). In some embodiments, the formulation does not contain a surfactant.

In some embodiments, the formulation further comprises a preservative, such as phenol, meta-cresol, or sodium benzoate.

In some embodiments, the PCSK9-binding fusion protein formulation consists essentially of (in addition to the active agent as described): L-Histidine, L-Histidine monohydrochloride, Sodium chloride, and Polysorbate-80. Exemplary embodiments are shown in the following Table 1:

| Component | Range | Exemplary embodiments (±10%) | Function |
|---|---|---|---|
| PCSK9-binding fusion protein | 100 to 300 mg/mL | 250 mg/mL 300 mg/mL | Active ingredient |
| L-Histidine | 1 to 5 mg/mL | 2.6 mg/mL | Buffering agent |

-continued

| Component | Range | Exemplary embodiments (±10%) | Function |
|---|---|---|---|
| L-Histidine monohydrochloride | 0.5 to 2 mg/mL | 0.7 mg/mL | Buffering agent |
| Sodium chloride | 2 to 20 mg/mL | 8.8 mg/mL | Isotonicity agent |
| Polysorbate-80 | 0.0 to 0.5 mg/mL | 0.2 mg/mL | Surfactant |

The pharmaceutical compositions of the disclosure may be conveniently presented in unit dose forms containing a predetermined amount of an active agent of the disclosure per dose.

In some embodiments, the composition is contained in an injection pen. Auto-injectors such as an "injection pen" are spring-loaded syringes designed to deliver a dose of a particular drug. By design, injection pens are easy to use and are intended for self-administration by patients, or administration by untrained personnel. Injection pens are designed to overcome the hesitation associated with self-administration of the needle-based drug delivery device. The injection pen keeps the needle tip shielded prior to injection and also has a passive safety mechanism to prevent accidental firing (injection). Injection depth can be adjustable or fixed and a function for needle shield removal may be incorporated. By pressing a button, the syringe needle is automatically inserted into the subcutaneous tissue and the drug is delivered. Once the injection is completed some injection pens have a visual or audible indication to confirm that the full dose has been delivered.

In some embodiments, the injection pen contains from 1 to 10 unit doses or from 1 to 5 unit doses. In some embodiments, the unit doses are no more than about 1.5 mLs or about 1 mL in volume (whether or not contained or delivered by an injection pen). In some embodiments, the unit doses are no more than 0.8 mL in volume, or no more than 0.7 mL in volume. In some embodiments, the injection pen delivers a microdose, e.g., having a volume in the range of about 50 µL to about 500 µL, or a volume in the range of from about 75 L to about 250 µL. In some embodiments, the microdose has a volume of from 100 to 200 µL. In various embodiments, the injection pen or other device for subcutaneous delivery provides a dose having from 30 to about 450 mg of the PCSK9-binding fusion protein. In various embodiments, the unit dose is from about 50 to about 400 mg, or from about 50 to about 300 mg. In some embodiments, the unit dose is at least 200 mg, or at least 250 mg, or at least 300 mg. In some embodiments, the unit dose is from about 250 mg to about 350 mg (e.g., about 300 mg). The amount of active agent delivered per unit dose can be adjusted based on the desired frequency of administration. For example, in some embodiments, a dose of from 20 to about 75 mg is administered as a weekly microdose (e.g., in a volume less than about 0.25 mL or less than about 0.15 mL). In other embodiments, a dose of from about 200 to about 450 mg is administered about every two weeks, monthly, or every other month, with a volume in the range of about 0.7 to 1.5 mL. In some embodiments, a dose of from about 275 mg to about 350 mg (e.g., about 300 mg) is administered every four weeks by subcutaneous injection, with a volume of about 1.5 mL or less or about 1 mL or less.

The composition or formulation is suitable for administration by subcutaneous, intramuscular, intradermal, or intravenous administration. The high concentration, relatively low viscosity and appropriate osmolality of the formulation allows for patient tolerability, less frequent dosing schedules and smaller volumes. As demonstrated herein, maximum PCSK9 suppression is achieved at a relatively low concentration of PCSK9-binding fusion protein, and higher concentrations allow for a longer duration of suppression. In some embodiments, the subject receives a unit dose of the composition about once every 1 week (e.g., by weekly administration of a microdose), or about once every 2 weeks, or about once every 3 weeks, or about once every 4 weeks (e.g., about once per month), or about once every 6 weeks, or about once every 8 weeks (about once every 2 months).

The composition may be administered for treating a PCSK9-related disorder in a human subject. PCSK9-related disorders are described in U.S. Pat. Nos. 8,420,098, 9,238, 027, and 9,856,306, which are hereby incorporated by reference in their entireties. In some embodiments, the patient is in need of a reduction in LDL (e.g., LDL-Cholesterol). In some embodiments, the subject may exhibit a cholesterol-related disease such as hypercholesterolemia and/or atherosclerosis. In various embodiments, the subject exhibits a condition selected from a lipid disorder, hypercholesterolemia, hyperlipoproteinemia, hyperlipidemia, dyslipidemia, coronary heart disease, atherosclerosis, and diabetes mellitus. In some embodiments, the subject has familial hypercholesterolemia. In some embodiments, the subject has or is at high risk of cardiovascular disease (e.g., atherosclerotic coronary heart disease).

Hypercholesterolemia is a condition characterized by elevated serum cholesterol. Elevated serum cholesterol levels affect a substantial fraction of the population and are an important risk factor for atherosclerosis and myocardial infarction. Cholesterol-lowering drugs such as HMG-COA reductase inhibitors ("statins") are conventionally administered to hypercholesterolemia patients. "Familial hypercholesterolemia" (FH) is a genetic disorder characterized by high cholesterol levels, specifically very high levels of low-density lipoprotein (e.g., LDL-Cholesterol), in the blood and early cardiovascular disease. For individuals with FH high cholesterol levels are less responsive to conventional cholesterol control methods (such as statin therapy).

FH is an autosomal dominant metabolic disorder characterized by a mutation or mutations in the LDL-receptor (LDL-R) gene or other genes involved in lipid regulation, markedly elevated LDL-C and premature onset of atherosclerosis. In some embodiments, the hypercholesterolemia is Homozygous familial hypercholesterolemia or HoFH which is a condition characterized by a mutation in both maternal and paternal LDL-R genes.

In some embodiments, the subject has heterozygous FH. Heterozygous FH is conventionally treated with statins, bile acid sequestrants, or other lipid lowering agents that lower cholesterol levels.

In some embodiments, the hypercholesterolemia is polygenic hypercholesterolemia which is a condition characterized by elevated cholesterol that results from the influence of a variety of genetic factors. In certain embodiments, polygenic hypercholesterolemia may be exacerbated by dietary intake of lipids.

In some embodiments, the composition is administered alongside statin therapy or other oral lipid-lowering therapy. The composition in such embodiments will provide for additive lowering of LDL-C. In some embodiments, the composition is provided as the sole therapy for hypercholesterolemia, that is, without statin therapy or other oral lipid lowering therapy. For example, in such embodiments, the subject may have a statin intolerance. "Statin intolerance" occurs when a patient is unable to continue the use of a statin due to the development of a side effect or abnormalities indicating liver function or muscle function (creatine kinase) following a blood test. In some embodiments, statin intolerance can be either partial (i.e., only some statins at some doses) or complete (i.e., all statins at any dose). In some embodiments, statin intolerance leads to muscle aches, pains, weakness, or cramps, (i.e., myalgias): occurring in up to 15% of treated patients.

Unless stated otherwise, the term "about" as used herein means+10% of the associated numerical value.

Embodiments of the invention will now be described by the following examples.

EXAMPLES

Example 1: PCSK9-binding Fusion protein and PK-PD Behavior

Figure 1:
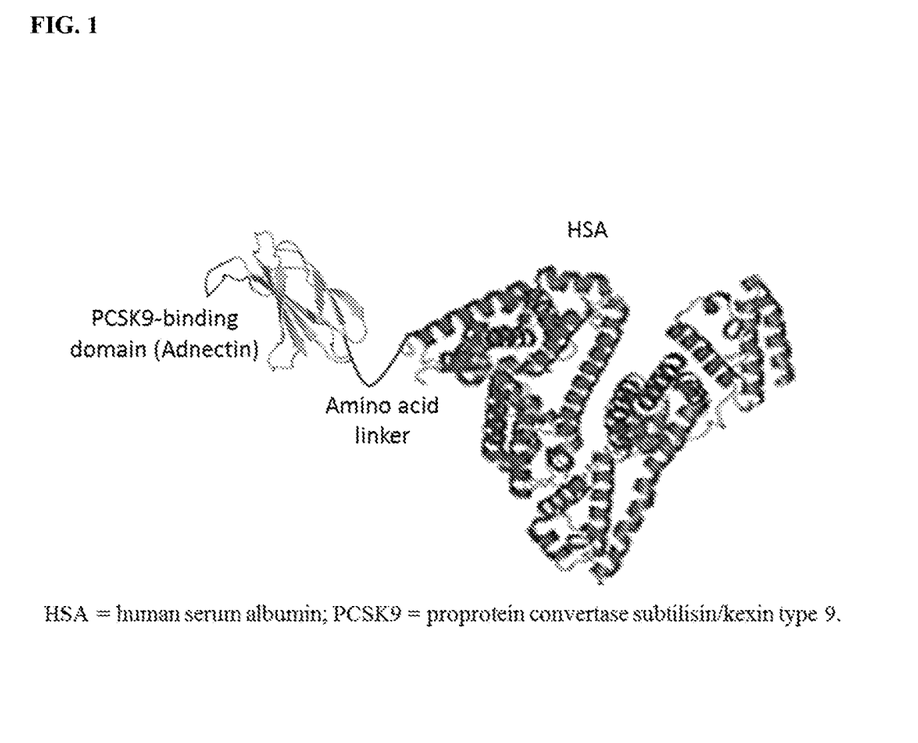
FIG. 1 illustrates the structure of the PCSK9-binding fusion protein.

The PCSK9-binding fusion protein comprises a modified fibronectin domain (adnectin) targeted against Proprotein Convertase Subtilisin/Kexin type 9 (PCSK9) and human serum albumin (FIG. 1). The fusion protein has a total molecular mass of approximately 77,000 Daltons. The PCSK9-binding fusion protein has high binding affinity for human PCSK9 and >100-fold weaker affinity for cynomolgus monkey PCSK9. Despite this difference in binding affinity the non-human primate (NHP) is considered an appropriate species for testing the safety and pharmacology of the PCSK9-binding fusion protein since maximum suppression of free PCSK9 and maximal LDL-C lowering is achieved in the NHP.

The PCSK9-binding fusion protein is being developed for subcutaneous (SC) administration for the treatment of, for example, hypercholesterolemia, including in patients with familial hypercholesterolemia or hypercholesterolemia and atherosclerotic coronary heart disease (CHD). The two main determinants of PCSK9-binding fusion protein PK are interaction with its target, PCSK9, and the ability to recycle via the neonatal Fc receptor (FcRn) and minimize renal filtration, thereby reducing PCSK9-binding fusion protein clearance and increasing half-life. Studies in wild-type mice cannot address the influence of either of these determinants on PCSK9-binding fusion protein PK, because the PCSK9-binding fusion protein does not effectively bind to mouse PCSK9, and HSA does not interact with mouse FcRn. Thus, the cynomolgus monkey provides the most suitable in vivo model for assessing PCSK9-binding fusion protein PK-PD, since binding to PCSK9 in this model results in a decrease in both free PCSK9 and LDL-C: in addition, HSA can efficiently recycle via the NHP FcRn receptor.

A hPCSK9 transgenic mouse was used to investigate the in vivo binding affinity of the PCSK9-binding fusion protein to hPCSK9 and the ability to recycle the PCSK9-binding fusion protein via hFcRn was also assessed in a hFcRn mouse. This human FcRn mouse model carries a null mutation for the mouse FcRn gene and a transgene expressing human FcRn α-chain under the control of its natural human promoter. Consequently, these mice serve as a model for evaluating pharmacokinetics of monoclonal antibodies and human serum albumin.

Figure 2A:
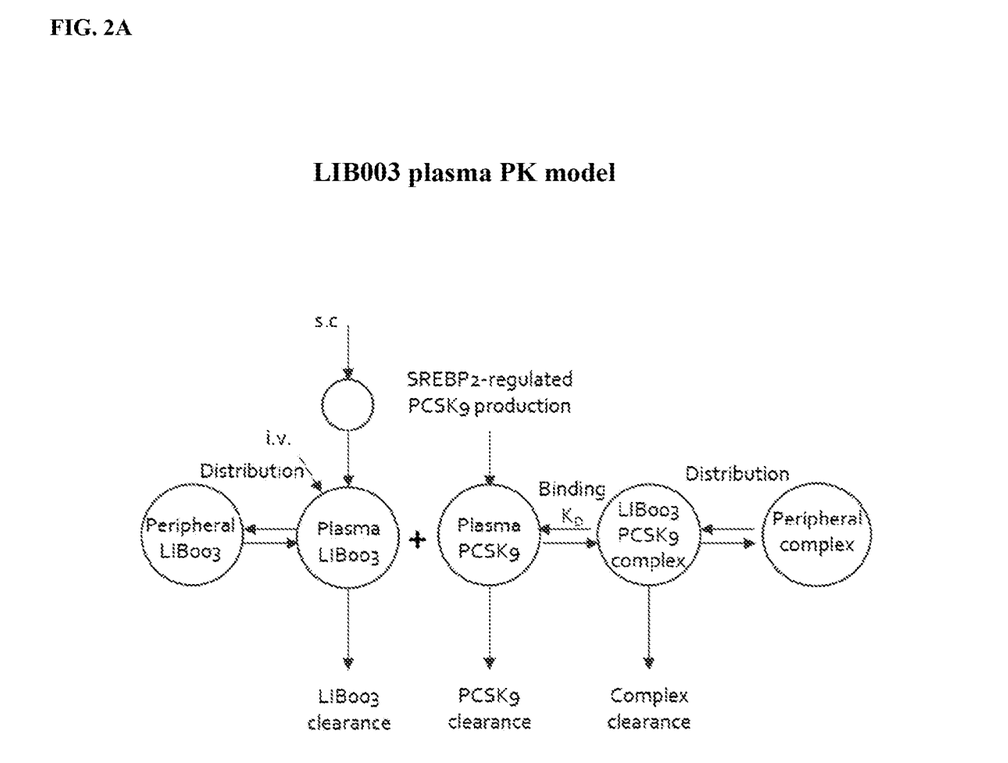
FIG. 2A illustrates the PCSK9 pharmacokinetics and pharmacodynamics (PK-PD) model in non-human primates (NHP) and humans. LIB-003 refers to the PCSK9-binding fusion protein.

There is a considerable dataset supporting the relationship between suppression of systemic free PCSK9 levels and the reduction of serum LDL-C for anti-PCSK9 antibodies. Gadkar K et al., A Mechanistic Systems Pharmacology Model for Prediction of LDL Cholesterol Lowering by PCSK9 Antagonism in Human Dyslipidemic Populations, CPT Pharmacometrics Syst. Pharmacol. 2014: 3 (11): 1-9; Squizzato A, et al., PCSK9 inhibitors for treating dyslipidemia in patients at different cardiovascular risk: a systematic review and meta-analysis. Intern. Emerg. Med. 2017: Jul:e1-11. See FIG. 2B. To estimate the human dose of the PCSK9-binding fusion protein (LIB003, SEQ ID NO: 3) required for achieving the desired target level of LDL-C reduction, allometric scaling of data from the above studies was incorporated into a translational semi-mechanistic model which included the known relationship between PCSK9 and LDL-C. FIG. 2A. The anticipated dose-effect relationship for LIB003 and serum LDL-C was constructed using this model.

TK-PD in Non-Human Primates

The TK-PD behaviour of LIB003 was characterized after intravenous (IV) and subcutaneous (SC) administration in a single dose non-GLP dose range finding (DRF) study (IV doses 10, 30, 100, 200 mg/kg: SC dose 200 mg/kg) and after repeated administration in GLP toxicity studies of 4-weeks (IV dose 100 mg/kg: SC doses 30 and 100 mg/kg) 12-weeks (SC doses 30 and 100 mg/kg), or 26-weeks (SC doses 30 and 100 mg/kg) duration.

The TK assay for LIB003 is constructed as a target-capture electrochemical luminescence assay, with hPCSK9 as the capture reagent and a ruthenium-labeled rabbit anti-HSA polyclonal antibody as the detection reagent. In NHP, the assay measures total LIB003 (due to the stronger affinity for the capture reagent, hPCSK9, compared with NHP PCSK9). Alternatively, the TK assay used a LIB003-specific mAb as the capture reagent and a ruthenium-labeled rabbit anti-HSA polyclonal antibody as the detection reagent. This assay format also measures total LIB003. Results from these studies indicate that in this dose range, after both intravenous and subcutaneous administration, the kinetics of total PCSK9-binding fusion protein are approximately linear and dose proportional.

In the DRF study, a persistent anti-drug antibody (ADA) response was present at all dose levels above 10 mg/kg. After a single dose of LIB003, the presence of ADAs in this study associated in most cases with a rapid loss of exposure to LIB003 and was preceded by a loss of target capture (reduced free PCSK9). Although ADAs were detected in most animals after weekly administration of the PCSK9-binding fusion protein (4-week, 12-week and 26-week GLP toxicity studies), exposure to the PCSK9-binding fusion protein was maintained throughout the dosing interval and the impact of ADAs on TK/PD was only apparent in two animals (4-week study), one animal (12-week study) and one animal (26-week study).

In the absence of an impact from ADAs, LIB003 is cleared slowly, and serum terminal half-life ranged from 8.3-10.4 days (mean 9 days) in the DRF study and 7.6-9.2 days (mean 8.3 days) in the recovery animals from the 4-week GLP tox study: consistent with the behaviour of an albumin-like molecule in non-human primates. Similar results were observed in the 12-week and 26-week GLP toxicity studies. In the DRF study, after single IV administration, clearance (CL) ranged from 5.63-7.65 mL/day/kg (mean 6.64 mL/day/kg) and volume of distribution (Vz) ranged from 67.6-103.8 mL/kg (mean 86.4 mL/kg) in animals in which this could be determined.

Total PCSK9 concentration (bound and unbound to LIB003) increased slowly with a peak occurring at about 7 days post-dose and at this time point total PCSK9 concentration is <10% of the circulating LIB003 concentration. Target-capture, as measured by free PCSK9 and LDL reduction, is maximal at all doses in the DRF study, indicating maximum target suppression at the lowest dose tested (10 mg/kg). Results indicate that in the absence of ADAs, increasing the dose of LIB003 increased the duration of maximal target capture.

Irrespective of either the dose or the route of administration, serum LDL was suppressed by about 60%, consistent with a maximal pharmacodynamic effect at all dose levels. As expected, the loss of LDL suppression and return to baseline levels was consistent with the loss of maximal PCSK9 capture. Overall, these studies demonstrate that the maximum pharmacodynamic effect has been achieved and higher doses would not give rise to greater suppression of either free PCSK9 or LDL.

After a subcutaneous dose $C_{max}$ was lower and $T_{max}$ occurred later compared with a slow IV bolus at the same dose level, indicative of absorption from the injection site into the systemic circulation. Absolute bioavailability for the subcutaneous route is estimated to be about 76% in the DRF study and 66.5-89.7% in the 4-week GLP toxicity study although both estimates are compromised by the presence of ADAs and an inability to characterize the total area under the curve (AUC) after subcutaneous administration. A combined analysis of both studies using a population PK model estimates bioavailability after subcutaneous administration to be 92% and is likely to be a more reliable estimate since the model generates an estimate of total AUC for both routes of administration.

Predicted PK-PD Behavior in Human

Data from multiple studies were combined to predict the expected PK-PD behaviour of LIB003 in human. Namely, a population 2-compartment PK-PD binding model describing the exposure to LIB003 and suppression of PCSK9 was constructed from NHP data (DRF study and 4wk GLP tox study). In scaling these parameters to human, the in vivo binding affinity to hPCSK9 was derived from PK-PD studies in hPCSK9 transgenic mouse. These data were adequately described by a one-compartment PK model since only data after subcutaneous administration are available; the model was otherwise equivalent to that used for the NHP data. The observed difference in LIB003 binding affinity for NHP PCSK9 and hPCSK9 was consistent for both the in vitro and in vivo derived data and the in vivo derived Kp value from the hPCSK9 transgenic mouse was used for the prediction to human.

TABLE 2

| Species | Binding affinity to PCSK9 in vitro (nM) | Binding affinity to PCSK9 in vivo (nM) |
|---|---|---|
| NHP | 8.1 | 56.4 |
| Human | 0.06 | 0.15 |

The clearance of LIB003 in both NHP and hFcRn mouse was consistent with the expected clearance of HSA in these animals and the clearance of LIB003 was therefore predicted to mimic the clearance of HSA in human (half-life 19 days: allometric exponent 0.74). Other parameters were scaled allometrically using the expected coefficients for a therapeutic albumin-fusion protein of approximately 77 kDa in size.

Figure 2B:
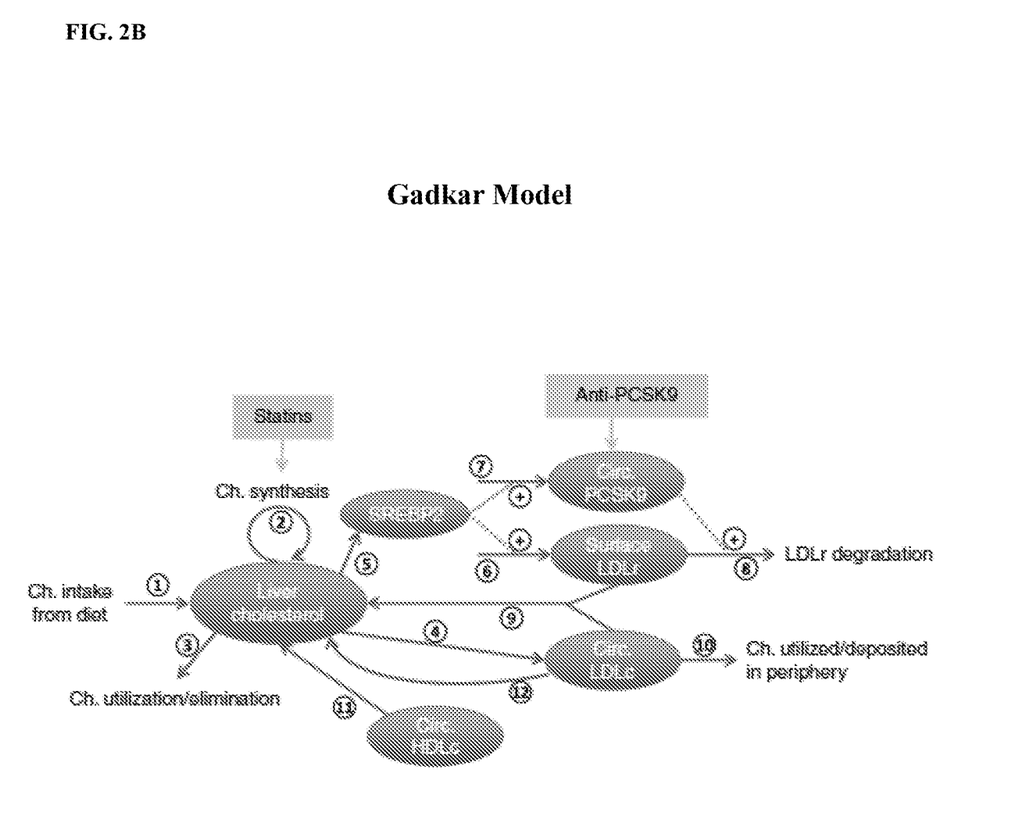
FIG. 2B illustrates the Gadkar model for predicting the effect of PCSK9 targeting on LDLC. Gadkar K et al., A Mechanistic Systems Pharmacology Model for Prediction of LDL Cholesterol Lowering by PCSK9 Antagonism in Human Dyslipidemic Populations, CPT Pharmacometrics Syst. Pharmacol. 2014: 3 (11).

The overall structure of the NHP and human PK-PD binding model describing the capture and suppression of free PCSK9 is shown in FIGS. 2A and 2B. A quantitative systems pharmacology model has previously been established to describe the mechanism of action of statins and an anti-PCSK9 antibody in human. Gadkar K et al., A Mechanistic Systems Pharmacology Model for Prediction of LDL Cholesterol Lowering by PCSK9 Antagonism in Human Dyslipidemic Populations, CPT Pharmacometrics Syst. Pharmacol. 2014: 3 (11). This model was employed to provide a link between the predicted suppression of PCSK9 in human and the reduction in LDL-C over time after single subcutaneous and intravenous doses of LIB003 in the First in Human (FIH) study.

Example 2: Formulation and Stability Evaluation

The performance of various buffers and excipients in the formulation of the PCSK9-binding fusion protein was assessed.

To ascertain the appropriate buffer and pH to use in the formulation, 18 different buffer and pH conditions using 6 different buffers at 2 mg/ml LIB003 were analyzed by DSC to assess thermal stability and DLS to assess aggregate formation. From these experiments, pHs lower than 5 and greater than 7 were eliminated due protein unfolding initiating at a temperature of <50° C. (Tonset) for those pH values.

The buffer/pH combinations analyzed are shown in Table 3 below. Combinations selected for further screening are shown by the pH value being bolded and underlined.

TABLE 3

| Buffer/pH Screen | |
|---|---|
| Buffer | pH |
| Acetate | 4.2 |
| pKa = 4.76 | 4.5 |
|  | 5.0 |
|  | 5.5 |
| Succinate | 4.2 |
| pKa = 5.64 | 4.5 |
|  | 5.0 |
|  | 5.5 |
|  | 6.5 |
| Citrate | 5.0 |
| pKa = 6.4 | 6.0 |
|  | 7.0 |
| Histidine | 6.0 |
| pKa = 6.04 | 7.0 |
| Phosphate | 6.5 |
| pKa = 7.2 | 7.5 |
| Tris | 7.5 |
| pKa = 8.1 | 8.0 |

Following identification of an acceptable pH range and appropriate buffer, excipients were investigated in combination with the defined buffers and pHs. In total, 15 different buffer/excipient combinations at 2 mg/mL LIB003 were prepared and analyzed by DSC to assess thermal stability and DLS to assess aggregate formation. Three of the buffer/excipient combinations were eliminated due to a Tonset of less than 55° C. Further, the DLS data suggested that the use of sucrose, sorbitol and low concentrations of NaCl led to aggregation and therefore their use was limited in subsequent formulations.

The buffer/excipient combinations analyzed are shown in Table 4 below. Combinations selected for further screening are shown by the excipient being bolded and underlined.

TABLE 4

Buffer/Excipient Screen

| Buffer/pH | Excipient |
|---|---|
| 20 mM Succinate, pH 5.5 | 50 mM NaCl |
| | 150 mM NaCl |
| | 150 mM Arginine |
| | 250 mM Sorbitol |
| | 250 mM Sucrose |
| 20 mM Citrate, pH 6.0 | 50 mM NaCl |
| | 150 mM NaCl |
| | 150 mM Arginine |
| | 250 mM Sorbitol |
| | 250 mM Sucrose |
| 20 mM Histidine, pH 7.0 | 50 mM NaCl |
| | 150 mM NaCl |
| | 150 mM Arginine |
| | 250 mM Sorbitol |
| | 250 mM Sucrose |

To determine suitable buffer and excipient combinations for maintaining stability of LIB003 formulated at high concentrations, solubility screening was performed on the 12 different formulations identified in Table 4 above. Theses formulations were concentrated to target concentrations of 200 mg/mL, 250 mg/mL, 300 mg/mL, and 340 mg/mL. Turbidity was equivalent across all of the formulations and no aggregation was observed when assessed by SEC-HPLC. Based on these parameters, these formulations were considered equivalent.

To evaluate the potential benefit of adding a surfactant to the LIB003 candidate formulations, eight buffer/excipient combinations from Table 4 were evaluated either with or without polysorbate 80 (PS80) for a total of 16 formulations at 250 mg/ml LIB003 (Table 5). Since PS80 can be effective at preventing aggregation and particulate formation, candidate formulations were evaluated for their ability to withstand repeated freeze-thaw and agitation stresses. No differences were observed based on recovery, turbidity, or aggregation propensities (evaluated by DLS and SEC). All formulations containing PS80 were progressed due to the anticipated benefit of PS80 upon long term storage and product handling.

TABLE 5

Buffer/Excipient and Surfactant Screen

| Buffer/pH | Excipient | Surfactant (PS80) |
|---|---|---|
| 20 mM Succinate, pH 5.5 | 150 mM NaCl | − |
| | | + |
| | 250 mM Sorbitol | − |
| | | + |
| | 250 mM Sucrose | − |
| | | + |
| 20 mM Citrate, pH 6.0 | 150 mM Arginine | − |
| | 20 mM Citrate, pH 6.0 | + |
| | 250 mM Sorbitol | − |
| | | + |
| | 250 mM Sucrose | − |
| | | + |
| | 150 mM NaCl | − |
| | | + |
| 20 mM Histidine, pH 7.0 | 150 mM NaCl | − |
| | | + |

The stability of LIB003 and lack of differentiation between formulations under normal storage conditions and shear stresses, even at high LIB003 concentrations, suggested that an alternative approach was required to identify a formulation for LIB003 that would withstand long-term storage conditions. The formulations identified from the buffer/excipient screen (Table 4) at target concentrations of 340 mg/mL were spiked with 0.02% PS80, stored at 2-8° C. or 50° C. for three weeks and analyzed by SEC-HPLC. In general, low levels of high molecular weight (HMW) and low molecular weight (LMW) species were observed after 3 weeks of storage at 50° C. Formulations containing citrate were narrowed to the excipients arginine and sorbitol based on the low percentage of HMW species in these formulations. Of the histidine formulations, 150 mM NaCl was chosen for additional experiments based on the highest percentage of main peak species. Lastly, succinate was eliminated from further consideration based on the increased levels of HMW and LMW species observed in most succinate formulations stored at 50° C. relative to the 2-8° C. comparator control sample.

The results of these analysis are shown in Table 6 below; the preferred formulations are illustrated by bold and underlined font.

TABLE 6

SEC-HPLC Evaluation of High Concentration LIB003 Stored at 50° C. for 3 weeks.

| Buffer/pH | Excipient | % HMW | % Main | % LMW |
|---|---|---|---|---|
| 20 mM Succinate, pH 5.5 | 150 mM NaCl | 3.1 | 96.2 | 0.8 |
| | 150 mM Arginine | 1.7 | 97.7 | 0.6 |
| | 250 mM Sorbitol | 3.9 | 95.4 | 0.7 |
| | 250 mM Sucrose | 3.3 | 96.1 | 0.6 |
| 20 mM Citrate, pH 6.0 | 50 mM NaCl | 1.8 | 97.9 | Below LOQ |
| | 150 mM NaCl | 2.0 | 97.6 | Below LOQ |
| | 150 mM Arginine | 1.1 | 98.3 | Below LOQ |
| | 250 mM Sorbitol | 1.1 | 98.6 | Below LOQ |
| | 250 mM Sucrose | 1.2 | 98.5 | Below LOQ |
| 20 mM Histidine, pH 7.0 | 50 mM NaCl | 2.6 | 97.0 | Below LOQ |
| | 150 mM NaCl | 1.0 | 98.6 | Below LOQ |
| | 150 mM Arginine | 1.0 | 98.3 | 0.8 |

HMW = high molecular weight; LMW = low molecular weight; LOQ = limit of quantitation; mM = millimolar; NaCl = sodium chloride.

To further explore candidate formulations, LIB003 was formulated at 250 mg/mL in the three buffer/excipient combination with PS80 at 3 different pHs (Table 7). The samples were stored at stored at 2-8° C. or 50° C. for three weeks to induce degradation and analyzed for LIB003 concentration/recovery (A280), particulates (DLS), aggregation (SEC-HPLC), charge profile (icIEF), clipping (CE-SDS), potency, turbidity and thermal stability (DSC). Comparison of the charge profiles, propensity for aggregation/particulate formation, and relative potency after storage at 50° C. for 3 weeks demonstrated some differentiation between the formulations (Tables 8, 9, 10 and 11). The CE-SDS profiles, recovery, turbidity and thermal stability were comparable across formulations.

TABLE 7

Candidate Formulations Prior to Storage

| Formulation | Target pH | Actual pH | Concentration (mg/mL) | SEC-HPLC % HMW | % Main | % LMW | icIEF % Acidic | % Main | % Basic |
|---|---|---|---|---|---|---|---|---|---|
| 20 mM Citrate, 150 mM Arginine, 0.02% PS80 | 5.5 | 5.6 | 274.4 | 0.8 | 99.2 | ND | 30.1 | 68.3 | 1.6 |
| | | 5.7 | 259.0 | 0.6 | 99.3 | ND | 30.2 | 68.1 | 1.7 |
| | 6.0 | 6.1 | 271.6 | 0.9 | 99.2 | ND | 30.8 | 67.4 | 1.8 |
| | | 6.1 | 254.1 | 0.8 | 99.2 | ND | 31.6 | 66.3 | 2.1 |
| | 6.5 | 6.5 | 260.2 | 0.9 | 99.1 | ND | 30.8 | 67.4 | 1.8 |
| | | 6.5 | 267.9 | 1.0 | 99 | ND | 31.1 | 67.1 | 1.8 |
| 20 mM Citrate, 250 mM Sorbitol, 0.02% PS80 | 5.5 | 5.6 | 259.6 | 0.8 | 99.2 | ND | 30.7 | 67.7 | 1.6 |
| | | 5.6 | 258.9 | 0.6 | 99.3 | ND | 32.7 | 65.5 | 1.8 |
| | 6.0 | 6.0 | 268.3 | 1.1 | 98.9 | ND | 31.1 | 67.3 | 1.6 |
| | | 6.0 | 271.0 | 0.8 | 99.2 | ND | 30.6 | 67.8 | 1.7 |
| | 6.5 | 6.5 | 266.8 | 1.0 | 99 | ND | 33.3 | 65.6 | 1.1 |
| | | 6.5 | 261.4 | 0.7 | 99.3 | ND | 30.7 | 67.7 | 1.6 |
| 20 mM Histidine, 150 mM NaCl, 0.02% PS80 | 6.0 | 6.0 | 248.7 | 0.7 | 99.3 | ND | 30.1 | 68.1 | 1.8 |
| | | 6.0 | 263.9 | 0.9 | 99.1 | ND | 31.3 | 66.3 | 2.4 |
| | 6.5 | 6.5 | 260.4 | 0.7 | 99.3 | ND | 31.6 | 66.1 | 2.4 |
| | | 6.5 | 260.5 | 0.9 | 99.2 | ND | 29.7 | 68.5 | 1.8 |
| | 7.0 | 6.9 | 267.3 | 0.9 | 99.1 | ND | 29.8 | 68.0 | 2.1 |
| | | 7.0 | 267.2 | 0.8 | 99.3 | ND | 30.1 | 68.1 | 1.9 |

ND = none detected

TABLE 8 icIEF Change in Charge Distribution after Storage at 50° C. for 3 Weeks

| | | Change in Charge Species (50° C. storage relative to 2-8° C.) | | |
|---|---|---|---|---|
| Formulation | pH | Acidic | Main | Basic |
| 20 mM Citrate, 150 mM Arginine, 0.02% PS80 | 5.6 | 0.8 | −22.0 | 21.2 |
| | 5.7 | 3.2 | −23.3 | 20.1 |
| | 6.1 | 4.6 | −8.3 | 3.7 |
| | 6.1 | 5.1 | −7.2 | 2.1 |
| | 6.5 | 6.9 | −11.1 | 4.3 |
| | 6.5 | 4.4 | −9.7 | 5.3 |
| 20 mM Citrate, 250 mM Sorbitol, 0.02% PS80 | 5.6 | −1.5 | −31.2 | 32.7 |
| | 5.6 | 2.4 | −30.3 | 27.9 |
| | 6.0 | 5.5 | −12.8 | 7.3 |
| | 6.0 | 6.0 | −12.8 | 6.8 |
| | 6.5 | 4.3 | −8.5 | 4.4 |
| | 6.5 | 6.8 | −9.1 | 2.3 |
| 20 mM Histidine, 150 mM NaCl, 0.02% PS80 | 6.0 | 2.6 | −19.5 | 16.7 |
| | 6.0 | 4.9 | −15.5 | 10.5 |
| | 6.5 | 9.2 | −10.7 | 1.4 |
| | 6.5 | 10.4 | −13.3 | 2.8 |
| | 6.9 | 10.3 | −11.6 | 1.4 |
| | 7.0 | 12.4 | −15.0 | 2.5 |

TABLE 9

SEC-HPLC Change in HMW and LMW Species after Storage at 50° C. for 3 Weeks

| | | 50° C. change from 2-8° C. | | |
|---|---|---|---|---|
| Formulation | pH | HMW | Main | LMW |
| 20 mM Citrate, 150 mM Arginine, 0.02% PS80 | 5.6 | 25.5 | −26.4 | 1.0 |
| | 5.7 | 20.7 | −21.7 | 1.0 |
| | 6.1 | 5.2 | −6.2 | 1.0 |
| | 6.1 | 4.8 | −5.8 | 1.0 |
| | 6.5 | 2.6 | −3.8 | 1.1 |
| | 6.5 | 2.5 | −3.2 | 0.7 |
| 20 mM Citrate, 250 mM Sorbitol, 0.02% PS80 | 5.6 | 42.0 | −42.5 | 0.5 |
| | 5.6 | 38.2 | −38.9 | 0.7 |
| | 6.0 | 12.3 | −13.1 | 0.8 |
| | 6.0 | 11.6 | −12.5 | 0.9 |
| | 6.5 | 4.2 | −5.0 | 0.8 |
| | 6.5 | 3.6 | −4.7 | 1.0 |
| 20 mM Histidine, 150 mM NaCl, 0.02% PS80 | 6.0 | 20.9 | −22.1 | 1.2 |
| | 6.0 | 16.5 | −17.4 | 0.9 |
| | 6.5 | 5.7 | −6.9 | 1.2 |
| | 6.5 | 6.4 | −7.5 | 1.1 |
| | 6.9 | 2.4 | −3.5 | 1.0 |
| | 7.0 | 3.9 | −5.2 | 1.3 |

TABLE 10

Potency as a Function of Storage Temperature

| | % Relative Potency | | Change in % Relative |
|---|---|---|---|
| Formulation | 2-8° C. | 50° C. | Potency |
| 20 mM Citrate, 150 mM Arginine, 0.02% PS80, pH 6.0 | 113.7 | 97.8 | −15.9 |
| | 93.5 | 80.2 | −13.3 |
| 20 mM Citrate, 250 mM Sorbitol, 0.02% PS80 pH 6.0 | 106 | 70.5 | −35.6 |
| | 103.4 | 75.1 | −28.3 |
| 20 mM Histidine, 150 mM NaCl, 0.02% PS80 pH 6.5 | 98.9 | 78.5 | −20.5 |
| | 100 | 82.1 | −17.9 |

Given the goal to deliver LIB003 in an 0.25-1.5 mL SC injection using an autoinjector with a 27G or smaller bore needle, additional experiments were performed in order to determine whether LIB003 formulated at 250 mg/mL would have properties suitable for SC injection via an autoinjector. The top three formulations at 250 mg/mL with the respective center point pH were evaluated for viscosity, osmolality and particulates. The targets were <15 cP for viscosity, 250-350 mOsm for osmolality, and particulate levels well below regulatory limits. Results are shown in Table 11 below. Particulate levels were comparably low across all formulations.

TABLE 11

Results of Viscosity and Osmolality Analysis

| Formulation | Prep | Osmolality (mOsm) | Viscosity (cP) | Concentration (mg/mL) |
|---|---|---|---|---|
| 20 mM Citrate 150 mM Arginine pH 6.0 | 1 2 | 355 365 | 11.5 14.4 | 250.2 266.0 |
| 20 mM Citrate 250 mM Sorbitol pH 6.0 | 1 2 | 415 420 | 17.5 16.9 | 254.5 267.8 |
| 20 mM Histidine 150 mM NaCl pH 6.5 | 1 2 | 335 329 | 10.2 11.3 | 242.8 269.0 |

The PCSK9-binding fusion protein was formulated as a sterile solution for injection (subcutaneous) in 20 mM histidine, 150 mM NaCl, 0.02% (w/v) polysorbate-80, pH 6.8 for additional stability studies. These stability studies included evaluations under long-term storage conditions, accelerated conditions as well as stressed conditions. The intended long-term storage temperature of PCSK9-binding fusion protein product is 5±3° C., and short-term storage (≤1-6 months) at 25° C.±3° C.

Stability data for 1 month was obtained at the intended storage temperature (5° C.±3° C.) as well as at the accelerated (25±2° C./60±5% RH) and stressed (40±2° C./75±5% RH) storage conditions.

For an exemplary PCSK9-binding fusion protein product lot, data for all evaluated parameters including stability indicating parameters (icIEF, potency, CE-SDS, and SEC-HPLC) in the stability protocol were within the acceptance criteria at the examined time point (1 month) and at each storage condition. Further, no major increase in aggregate or degradant species, or decrease in potency was observed for long-term storage condition. A slight increase in aggregates (~1%), was observed by SEC-HPLC for the accelerated and stress conditions, however, the results are well within the acceptance criteria for main peak by SEC-HPLC and no change in potency was observed. Also, a slight increase in fragments (~2%) was observed by reduced CE-SDS at the stress condition but again, concomitant change in potency was not observed. A small increase (~1-4%) in acidic charge variant species with a concomitant decrease in main peak species was observed by icIEF at each storage condition, (of note, an opposite trend was observed for drug substance indicating that perhaps, the changes observed are within the variability of the method). No changes in appearance, physicochemical parameters or potency were observed. Taken together, the stability data demonstrate that the PCSK9-binding fusion protein product is stable for 1 month at the long-term, accelerated and stressed storage conditions evaluated.

Additionally, long-term stability data for 18 months was obtained at the intended storage temperature (5° C.+3° C.) as well as for 9 months at the accelerated storage condition (25+2° C./60+5% RH) and for three months at the stressed (40+2° C./75+5% RH) storage condition.

For an exemplary PCSK9-binding fusion protein product lot, data for all evaluated parameters including stability indicating parameters (icIEF, potency, CE-SDS, and SEC-HPLC) in the stability protocol were within the acceptance criteria at the examined time points and at each storage condition. Further, no major increase in aggregate or degradant species, nor decrease in potency was observed for long-term storage condition. A slight increase in aggregates (~1%), was observed by SEC-HPLC at all storage conditions, however, the results were well within the acceptance criteria for main peak by SEC-HPLC and no change in potency was observed (within assay variability). Also, a slight increase in fragments (up to ~2%) was observed by reduced CE-SDS at the long-term storage condition but again, a corresponding change in potency was not observed and may be considered to be within the variability of the method. The increase in fragments by reduced and non-reduced CE-SDS correlated with increased time and temperature (up to ~5% change at the stressed condition). A fluctuation (up to ~8%) of acidic and main peak species by icIEF was observed at the long-term storage condition, however, the fluctuations are within the variability of the method. icIEF results at the accelerated and stressed conditions initially appeared to indicate a potential positive trend for acidic species (up to ~7%) and a corresponding negative trend for main peak species, though a concomitant change in potency was not observed. However, additional time points indicate that the observed small changes may also have been fluctuations related to method variability. Sub-visible particles appear to fluctuate slightly over time but are well within the acceptable limits (of note, an atypical result was observed for particles >2 μm and >5 μm at 9 months at both the long-term and accelerated condition: however, the particles counts returned to an expected level at the 12 month and 18 month time points). No changes in appearance, physicochemical parameters, or potency were observed.

Further, long-term stability data for 12 months was obtained at the intended storage temperature (5° C.+3° C.) as well as for 12 months at the accelerated storage condition (25+2° C./60+5% RH).

For an exemplary PCSK9-binding fusion protein product lot, data for all evaluated parameters including stability indicating parameters (icIEF, potency, CE-SDS, and SEC-HPLC) in the stability protocol were within the acceptance criteria at the examined time points and at each storage condition. Further, no major increase in aggregate or degradant species, nor decrease in potency were observed for long-term storage condition. A slight increase in aggregates (up to ~1%) was observed by SEC-HPLC at both storage conditions, however, the results were well within the acceptance criteria for main peak by SEC-HPLC and no change in potency was observed (within assay variability). Also, a slight increase in fragments at the long-term storage (up to ~2%) and at the stressed storage condition (~3%) was observed by reduced CE-SDS condition and by non-reduced CE-SDS at the stressed storage condition (~3%) but again, a corresponding change in potency (within the assay variability) was not observed. An increase in acidic charge variant species (up to ~5%) with a concomitant decrease in main peak species was observed by icIEF at both storage conditions (which may be attributed to assay variability since later time points had lower percent acidic species). No changes in appearance, physicochemical parameters, or potency were observed.

Example 3: First in Human Study

LIB003 has been studied in a Phase 1 SAD study of 63 subjects aged ≥18 and ≤70 years of age, 24 females and 39 males, 45 on LIB003 and 18 placebo, monitored post dose for at least 43 days. The study was placebo controlled and double-blind. In each of the 9 cohorts there were 7 subjects: 5 LIB-003 and 2 placebo-treated patients resulting in 43 subjects treated with LIB003 and 18 with placebo. Subcutaneous doses of LIB003 25 mg. 75 mg, 150 mg. 300 mg, and 600 mg were administered to healthy subjects on stable diet with no lipid-lowering therapy and baseline LDL-C ≥100 and ≤190 mg/dL. The 150 mg and 300 mg doses were also administered SC to patients on stable statin therapy with baseline LDL-C ≥100 mg/dL. All subjects had TG≤250 mg/dL. Two additional cohorts of healthy subjects not on lipid-lowering therapy with the same lipid entry criteria as their SC cohorts received LIB003 300 mg and 600 mg IV.

Overview of Safety Results

All 63 subjects completed the study with no patients dropping out or terminating prior to Day 43. Overall, LIB003 was safe and well tolerated following both single SC and IV dosing in healthy subjects and in patients with hypercholesterolemia on statin therapy.

Overview of Pharmacodynamic (Efficacy) Results

Mean reductions in free PCSK9 were rapid with all doses, and reached more than 99% within 12 hours and were sustained in virtually all subjects for at least 3 weeks (Day 22) in the cohorts not on lipid-lowering therapy receiving ≥150 mg of LIB003. While the LIB003 300 mg dose maintained 99% suppression of free PCSK9 for 29 days, in the 150 mg dose subjects not on lipid-lowering therapy, free PCSK9 had decreased to 12% and in those on statins to 54% of baseline. The lower reductions in free PCSK9 were reflected in the decreases of LDL-C and apo B where larger reductions were maintained in subjects not on lipid-lowering therapy. However, these were not sustained through 4 weeks (Day 29) in patients on statins. The single 300 mg dose, in both non-statin and statin-treated subjects, provided more stable and maximal reductions in free PCSK9, LDL-C, and apo B. In addition, based on prior data from studies with mAbs, it is anticipated that multiple dosing will result in longer duration of both free PCSK9 suppression and LDL-C reduction. Furthermore, extensive prior data shows that patients on high intensity statins and those with FH have higher baseline PCSK9 levels and likely increased synthesis of PCSK9, and will require 300 mg or higher doses in order to suppress both free PCSK9 and LDL-C fully for 4 weeks.

Overview of Pharmacokinetic Results

The $C_{max}$, $AUC_{0-t}$, and $AUC_{inf}$ for total LIB003 from an SC dose increased in a dose-proportional manner between 75 mg and 300 mg of LIB003 and exhibited minor supra-dose proportionality between 25 mg-75 mg (4- to 5-fold increase) and 300 mg-600 mg (3-fold increase). Similarly, statin-treated subjects exhibited dose-proportional increases in total LIB003 over the 150 mg to 300 mg dose range, although the exposure of total LIB003 ($AUC_{0-t}$ and $AUC_{inf}$) were in general lower than exposures in the non-statin-treated subjects. The $C_{max}$, $AUC_{0-t}$, and $AUC_{inf}$ for total LIB003 administered IV increased dose proportionally.

The median $T_{max}$ of total LIB003 ranged from 72 to 168 hours (range was variable: 36 to 220 hours) across all SC dose levels. The T-HALF, CL/F, and Vz/F were also all similar across the SC doses tested as well as when LIB003 was administered with statins. The median $T_{max}$ of total LIB003 ranged from 0.33 to 1.08 hours across both IV dose levels. T-HALF, CL, and Vz were all similar across both IV doses tested.

Absolute bioavailability of total LIB003 ranged from 67% to 111% following single SC doses of 300 mg and 600 mg of LIB003, respectively.

Rationale for Phase 2 Study Dose Levels

Based on the free PCSK9 and LDL-C data from Phase 1 and objective of obtaining dosing at least Q4W in a volume that is consistent with a single SC injection with an auto-injector (≤1.5 mL), a Phase 2 dose-finding study in approximately 80 patients with ASCVD, or at high risk for ASCVD, or HeFH without CVD, on stable statin and/or ezetimibe is planned. The doses selected for Q4W dosing in this Phase 2, dose-finding study include 150 mg, 300 mg, and 350 mg. All 3 doses are anticipated to be safe based on the lack of findings at both human LIB003 exposure in Phase 1 up to 600 mg both SC and IV and levels achieved in the 12-week non-human primate GLP toxicology study.

Example 4: Randomized Double-Bind. Placebo-Controlled, Phase 2. Dose-Finding to Evaluate the Efficacy and Safety of LIB003 in Patients on Stable Lipid-Lowering Therapy Requiring Additional LDL-C Reduction LIB003 was studied in a 12 week randomized, double-blind, placebo-controlled, dose-finding Phase 2 study, which was followed by a four-week follow-up assessment period, to assess the percent change from baseline in LDL-C level as the mean of weeks 10 and 12 and at week 12, as calculated by the Friedewald formula, with monthly (Q4W) dosing of various doses of LIB003. The study involved a total of 81 men and women aged ≥18 years of age with either atherosclerotic cardiovascular disease (ASCVD) or at high ASCVD risk (>10% 5-year or >7.5% 10-year risk) and for subjects with ASCVD or CVD risk a calculated LDL-C of ≥80 mg/dL, or for subjects with heterozygous familial hypercholerstolemia and no CVD a calculated LDL-C of ≥100 mg/dL. All of the subjects had a TG of ≤400 mg/dL on stable lipid-lowering oral drug therapy, such as a statin with or without ezetimibe. These subjects were grouped into 3 active and 1 matching placebo treatment groups. In each group there were three LIB003 subjects that were randomized for every one placebo subject, i.e. 20 LIB003 subjects per treatment group and 20 placebo). Subcutaneous doses of 150 mg, 300 mg, or 350 mg LIB003 or placebo were administered subcutaneously monthly (Q4W) to subjects with hypercholesterolemia on a stable diet and oral LDL-C lowering drug therapy.

A summary of the demographics of the subjects enrolled in this study is shown in Table 11 below.

TABLE 11

| | Demographics of Subject Cohorts | | | |
|---|---|---|---|---|
| Treatment Group | Placebo | LIB003 150 mg Q4W | LIB003 300 mg Q4W | LIB003 350 mg Q4W |
| Number of patients | N = 20 | N = 21 | N = 19 | N = 21 |
| Age: mean (SD) years | 66.6 (7.4) | 65 (13) | 61.9 (10) | 65.5 (7.1) |

TABLE 11-continued

Demographics of Subject Cohorts

| Treatment Group | Placebo | LIB003 150 mg Q4W | LIB003 300 mg Q4W | LIB003 350 mg Q4W |
|---|---|---|---|---|
| Gender: male/female | 10/10 | 12/9 | 10/9 | 6/15 |
| Ethnicity: Caucasian/African-American | 14/6 | 15/6 | 12/7 | 19/2 |
| BMI (kg/m2) mean (SD) | 29.6 (4.6) | 31.1 (4.6) | 29.6 (3.3) | 29.4 (5.4) |
| Cardiovascular disease N (%) | 9 (45%) | 10 (48%) | 7 (37%) | 10 (48%) |
| Diabetes Mellitus N(%) | 8 (40%) | 11 (52%) | 10 (53%) | 10 (48%) |
| Current statin use N(%) | 16 (80%) | 18 (86%) | 12 (63%) | 19 (91%) |
| Baseline LDL-C* (mean ± SD) mg/dL | 119.2 (34) | 119.5 (37.5) | 128.9 (39.3) | 115.7 (30.5) |

*Calculated Friedewald formula

Overview of Safety Results

Overall, LIB003 was safe and generally well tolerated as a subcutaneous dose up to 350 mg Q4W in this study. All LIB003 doses, 150 mg, 300 mg, and 350 mg, were well tolerated and did not reveal any safety concerns. Of the 81 subjects, 79 subjects completed the study and two subjects discontinued. The discontinuations were not due to adverse events. Additionally, no adverse events led to a death in this study.

A summary of the treatment emergent adverse events (TEAEs) experienced by the subjects during the study is shown in Table 12 below.

TABLE 12

Subject TEAEs During Study

| Treatment Group | Placebo | LIB003 150 mg Q4W | LIB003 300 mg Q4W | LIB003 350 mg Q4W |
|---|---|---|---|---|
| Treatment Emergent Adverse Events (TEAEs) | 10 (50%) | 9 (42.9%) | 11 (58%) | 13 (62%) |
| Drug-related TEAEs | 2 (10%) | 1 (4.3%) | 1 (5.2%) | 2 (9.5%) |

A total of 43 out of 81 (53%) subjects had a TEAE, with 10 out of 20 (50%) on placebo and 33 out of 61 (54%) in the combined LIB003-treated groups. The majority of TEAEs were mild to moderate in severity. The most commonly reported TEAEs were fatigue, injection site bruising, upper respiratory tract infection, and dyspnea. All other TEAEs were reported by ≤3 subjects.

Only six out of 81 (7%) subjects had a study drug-related TEAE, with two out of 20 (10%) on placebo and four out of 61 (7%) in the combined LIB003-treated groups. The majority of study drug-related TEAEs were mild in severity: none were considered severe. The most commonly reported study drug-related TEAE was injection site erythema. All other study drug-related TEAEs were reported by ≤1 subject.

Six out of 81 (7%) subjects had an SAE, one (5%) on placebo and five (8%) in the combined LIB003-treated groups: none of which were considered related to the study drug. Five SAEs, one (5%) on placebo and four (7%) in the combined LIB003-treated groups were severe and one (2%) in the LIB003-treated group was moderate in intensity.

There were no TEAEs related to abnormal laboratory values. There were no clinically meaningful increases or trends in liver function tests (ALT, AST, or bilirubin) in any treatment group or differences between placebo or LIB003-treated groups. Specifically, no subject experienced an increase in ALT or AST>3×ULN and none had a bilirubin >2×ULN. A number of subjects in all treatment groups experienced non-sustained increases in CK, which were exercise- or activity-related and none exceeded 5×ULN. There were no clinically significant increases or differences between treatment groups in renal function, glucose, other chemistry or hematology parameters.

There were no clinically meaningful findings in the vital sign, ECG, and physical examination results. In total, there were five recorded incidents of injection site erythema at a 15-minute post-dose time point following study drug administration. One subject in the placebo group also reported injection site itching 15 minutes post-dose on day one. All injection site reactions that occurred 15 minutes post-dose were mild in severity with one in the placebo group and 4 in the combined LIB003-treated groups.

Overview of Efficacy Results

All tested LIB003 doses, 150 mg, 300 mg, and 350 mg, induced rapid, sustained, and significant mean decreases in LDL-C and free PCSK9 levels. The greatest mean decreases in LDL-C were observed in the 300 mg LIB003 dose cohort. Consistent with previous studies, the higher 350 mg LIB003 dose did not produce further LDL-C reduction. The 150 mg dose was found to be insufficient to obtain maximal LDL-C reduction for the full four weeks between doses.

A summary of the efficacy data from the study is shown in Table 13 below.

TABLE 13

Efficacy Data

| Treatment Group | Placebo | LIB003 150 mg Q4W | LIB003 300 mg Q4W | LIB003 350 mg Q4W |
|---|---|---|---|---|
| LDL-C mean (SD) % change at week 12* | 7.3 (21.3) | 26.4 (24.1) | 71 (17.7) | 62.8 (19.5) |
| LDL-C mean (SD) % change at week 12¨ | 5.7 (20.3) | 24.7 (25) | 66.2 (16.8) | 62.2 (16.7) |
| Apolipo-protein B % change at week 12 | 5.2 (13.2) | 22.4 (22.7) | 54.0 (16.0) | 53.0 (11.7) |
| Week 10/Week 12 LOCF¥ | | | | |
| LIB003 vs. Placebo LS Mean (SE) | | 48.0 (5.37)△ | 76.1 (5.51)△ | 67.0 (5.37)△ |
| 95% CI | | (−58.7, −37.3) | (−87.1, −65.1) | (−77.7, −56.3) |
| Week 12 LOCF¥ | | | | |
| LIB003 vs. Placebo LS Mean (SE) | | 33.5 (6.80)△ | −77.3 (6.97)△ | −67.1 (6.80)△ |
| 95% CI | | (−47.0, −19.9) | (−91.2, −63.5) | (−80.6, −53.6) |

*Calculated Friedewald formula
¨By ultracentrifugation
¥Co-primary endpoint (ANOVA)
△p-value < 0.0001

There was a large, sustained mean decrease in LDL-C levels from baseline to the average of weeks 10 and 12 LOCF and to week 12 LOCF, as calculated by the Friedewald formulate, following dosing within LIB003. The maximal LS mean percent change difference (95% CI) between LIB003 cohorts and the placebo group in LDL-C from baseline to the average of weeks 10 and 12 LOCF and to week 12 LOCF occurred in the 300 mg LIB003 dose cohort and was-76.1% ([−86.0%, −66.2%], p<0.0001) and −77.3% ([−90.5%, −64.1%], p<0.0001), respectively. Assessment of the mean percent change in LDL-C levels by preparative ultracentrifugation and the Hopkins formula yielded similar findings.

Consistent with previous studies showing that once maximal suppression of PCSK9 is achieved, no additional LDL-C reduction occurs, the higher dose of 350 mg of LIB003 did not produce an additional reduction in LDL-C levels. Although the 150 mg dose achieved similar reductions as the 300 mg and 350 mg doses every two weeks post-dose, it was insufficient to maintain maximal LDL-C reductions for the full four weeks between doses.

There was a large, sustained mean decrease in the free PCSK9 level from baseline to the average of weeks 10 and 12 LOCF and to week 12 LOCF following LIB003 doses. The LS mean percent change difference (95% CI) between LIB003 cohorts and the placebo group in the free PCSK9 level from baseline to the average of weeks 10 and 12 LOCF and to week 12 LOCF occurred in the 300 and 350 mg cohorts, which was −89.7% ([−100.0%, −79.4%], p<0.0001) and −92.8% ([−102.9%, −82.6%], p<0.0001), respectively. The LS mean percent change difference (95% CI) between LIB003 cohorts and the placebo group in the free PCSK9 level from baseline to Week 12 LOCF was −84.1% ([−99.5%, −68.7%], p<0.0001) and −90.2% ([−105.4%, −75.0%], p<0.0001) for the 300 and 350 mg cohorts, respectively. Although the 350 mg LIB0003 dose suppressed slightly more PCSK9 than the 300 mg dose at week 12 (90.2% versus 84.1%, respectively), this did not result in a greater LDL-C efficacy.

Additionally, there was a large and sustained mean increase in the total PCSK9 level from baseline to the average of weeks 10 and 12 LOCF and to week 12 LOCF following LIB003 doses. The mean percent change from baseline to the average of weeks 10 and 12 LOCF was 95.555%, 90.273%, and 90.080% for the LIB003 150 mg, 300 mg, and 350 mg cohorts, respectively. The mean percent change from baseline to week 12 LOCF was 75.165%, 78.188%, and 86.811% for the LIB003 150 mg, 300 mg, and 350 mg cohorts, respectively. In contrast, the placebo showed a minimal mean percent change (≤3.044%) at the same time points.

Further, there was a large, sustained mean decease in non-HDL-C levels, and a moderate and sustained mean decrease in TC levels from baseline to the average of weeks 10 and 12 LOCF and to week 12 LOCF. However, in both the LIB003 cohorts and the placebo group, there were only minimal mean changes in the HDL-C levels from baseline to the average of weeks 10 and 12 LOCF and to week 12. Additionally, a comparison of the percent change in VLDL-C and TG levels between each LIB003 cohort and the placebo group using an ANOVA model showed a small mean decrease in VLDL-C and TG levels from baseline to the average of weeks 10 and 12 LOCF and to week 12 LOCF.

Also, there was a large and sustained mean decrease in apo B levels from baseline to week 12 LOCF following LIB003 doses. The maximal LS mean percent change difference (95% CI) between LIB003 cohorts and the placebo group in apo B occurred for the 300 mg cohort and was-58.4% ([−68.9%, −48.0%], p<0.0001).

Moreover, there was a moderate and sustained decrease in the Lp (a) level from baseline to week 12 LOCF following all LIB003 doses. The maximal LS mean percent change difference (95% CI) between LIB003 cohorts and the placebo group in Lp (a) occurred for the 300 mg cohort and was-28.7% ([−42.6%, −14.8%], p<0.0001). This reduction is consistent with that achieved by PCSK9 monoclonal antibodies at equivalent doses and dosing frequency, which suppressed free PCSK9 and LDL-C similarly to LIB003 300 mg Q4W.

The apo A1 levels showed minimal mean change from baseline to week 12 LOCF for the LIB003 cohorts and the placebo group.

Based on the data from the Phase 2 study discuss above, the LIB003 300 mg subcutaneous Q4W dose was selected for open-label extension and Phase 3 studies.

SEQUENCE LISTING

```
Sequence total quantity: 4
SEQ ID NO: 1            moltype = AA   length = 96
FEATURE                 Location/Qualifiers
REGION                  1..96
                        note = PCSK9-binding motif
source                  1..96
                        mol_type = protein
                        organism = synthetic construct
SEQUENCE: 1
VSDVPRDLEV VAATPTSLLI SWDAPAEGYG YYRITYGETG GNSPVQEFTV PVSKGTATIS   60
GLKPGVDYTI TVYAVEFDFP GAGYYHRPIS INYRTE                            96

SEQ ID NO: 2            moltype = AA   length = 585
FEATURE                 Location/Qualifiers
source                  1..585
                        mol_type = protein
                        organism = Homo sapiens
SEQUENCE: 2
DAHKSEVAHR FKDLGEENFK ALVLIAFAQY LQQAPFEDHV KLVNEVTEFA KTCVADESAE   60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGKKLVAASQ AALGL                 585

SEQ ID NO: 3            moltype = AA   length = 687
FEATURE                 Location/Qualifiers
REGION                  1..687
                        note = PCSK9-binding polypeptide
source                  1..687
                        mol_type = protein
                        organism = synthetic construct
SEQUENCE: 3
VSDVPRDLEV VAATPTSLLI SWDAPAEGYG YYRITYGETG GNSPVQEFTV PVSKGTATIS   60
GLKPGVDYTI TVYAVEFDFP GAGYYHRPIS INYRTEGSGS GSDAHKSEVA HRFKDLGEEN  120
FKALVLIAFA QYLQQAPFED HVKLVNEVTE FAKTCVADES AENCDKSLHT LFGDKLCTVA  180
TLRETYGEMA DCCAKQEPER NECFLQHKDD NPNLPRLVRP EVDVMCTAFH DNEETFLKKY  240
LYEIARRHPY FYAPELLFFA KRYKAAFTEC CQAADKAACL LPKLDELRDE GKASSAKQRL  300
KCASLQKFGE RAFKAWAVAR LSQRFPKAEF AEVSKLVTDL TKVHTECCHG DLLECADDRA  360
DLAKYICENQ DSISSKLKEC CEKPLLEKSH CIAEVENDEM PADLPSLAAD FVESKDVCKN  420
YAEAKDVFLG MFLYEYARRH PDYSVVLLLR LAKTYETTLE KCCAAADPHE CYAKVFDEFK  480
PLVEEPQNLI KQNCELFEQL GEYKFQNALL VRYTKKVPQV STPTLVEVSR NLGKVGSKCC  540
KHPEAKRMPC AEDYLSVVLN QLCVLHEKTP VSDRVTKCCT ESLVNRRPCF SALEVDETYV  600
PKEFNAETFT FHADICTLSE KERQIKKQTA LVELVKHKPK ATKEQLKAVM DDFAAFVEKC  660
CKADDKETCF AEEGKKLVAA SQAALGL                                     687

SEQ ID NO: 4            moltype = AA   length = 6
FEATURE                 Location/Qualifiers
source                  1..6
                        mol_type = protein
                        organism = synthetic construct
SEQUENCE: 4
GSGSGS                                                              6
```

What is claimed is:

1. A proprotein convertase subtilisin kexin type 9 (PCSK9)-binding fusion protein comprising the amino acid sequence of SEQ ID NO: 3.

2. A composition comprising the PCSK9-binding fusion protein of claim 1, wherein the concentration of the fusion protein is at least 200 mg/mL.

3. The composition of claim 2, wherein the concentration of the fusion protein is at least 250 mg/mL.

4. The composition of claim 2, wherein the concentration of the fusion protein is at least 300 mg/mL.

5. A proprotein convertase subtilisin kexin type 9 (PCSK9)-binding fusion protein consisting of the amino acid sequence of SEQ ID NO: 3.

6. A composition comprising the PCSK9-binding fusion protein of claim 5, wherein the concentration of the fusion protein is at least 200 mg/mL.

7. The composition of claim 6, wherein the concentration of the fusion protein is at least 250 mg/mL.

8. The composition of claim 6, wherein the concentration of the fusion protein is at least 300 mg/mL.

* * * * *